United States Patent
Zhang et al.

(10) Patent No.: US 9,476,994 B2
(45) Date of Patent: Oct. 25, 2016

(54) VIRTUAL FRAMES FOR DISTRIBUTED LIST-MODE TIME-OF-FLIGHT RECONSTRUCTION WITH CONTINUOUS BED MOVEMENT

(71) Applicant: KONINKLIJKE PHILIPS N.V., Eindhoven (NL)

(72) Inventors: Bin Zhang, Cleveland, OH (US); Chi-Hua Tung, Aurora, OH (US); John Patrick Collins, Cleveland Heights, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 29 days.

(21) Appl. No.: 14/418,486

(22) PCT Filed: Jul. 31, 2013

(86) PCT No.: PCT/IB2013/056301
§ 371 (c)(1),
(2) Date: Jan. 30, 2015

(87) PCT Pub. No.: WO2014/024099
PCT Pub. Date: Feb. 13, 2014

(65) Prior Publication Data
US 2015/0260857 A1    Sep. 17, 2015

Related U.S. Application Data

(60) Provisional application No. 61/681,659, filed on Aug. 10, 2012.

(51) Int. Cl.
G01T 1/20    (2006.01)
G01T 1/29    (2006.01)
G01T 1/164    (2006.01)
G06T 11/00    (2006.01)
A61B 6/03    (2006.01)

(52) U.S. Cl.
CPC ............ *G01T 1/2985* (2013.01); *A61B 6/037* (2013.01); *G01T 1/1647* (2013.01); *G06T 11/005* (2013.01)

(58) Field of Classification Search
CPC .... G01T 1/2985; G06T 11/005; A61B 6/037
USPC .......................................................... 250/362
See application file for complete search history.

(56) References Cited

U.S. PATENT DOCUMENTS

| | | | |
|---|---|---|---|
| 7,638,771 B2 | 12/2009 | Breeding et al. | |
| 2003/0161521 A1 | 8/2003 | Newport et al. | |
| 2006/0081784 A1 | 4/2006 | Ross et al. | |
| 2010/0074498 A1 | 3/2010 | Breeding et al. | |
| 2010/0303319 A1* | 12/2010 | Wang | G06T 11/006 382/131 |
| 2011/0079722 A1 | 4/2011 | Gagnon | |

FOREIGN PATENT DOCUMENTS

WO    2006064401 A2    6/2006

* cited by examiner

Primary Examiner — David Porta
Assistant Examiner — Abra Fein

(57) ABSTRACT

A positron emission tomography (PET) system includes a memory (18), a subject support (3), a categorizing unit (20), and a reconstruction unit (22). The memory (18) continuously records detected coincident event pairs detected by PET detectors (4). The subject support (3) supports a subject and moves in a continuous movement through a field of view (10) of the PET detectors (4). The categorizing unit (20) categorizes the recorded coincident pairs into each of a plurality of spatially defined virtual frame (14). The reconstruction unit (22) reconstructs the categorized coincident pairs of each virtual frame into a frame image and combines the frame images into a common elongated image.

21 Claims, 4 Drawing Sheets

Figure 1:
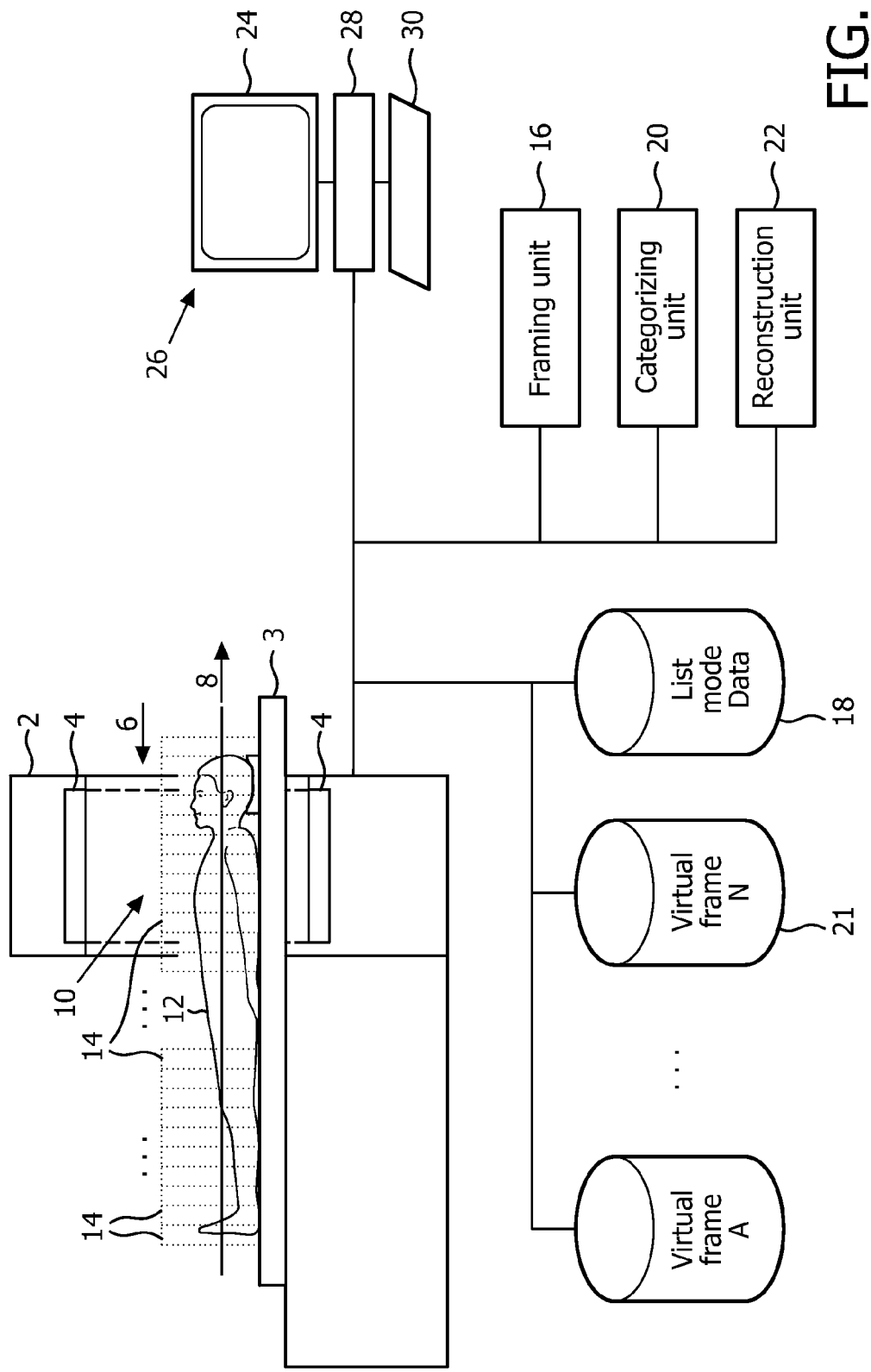

VIRTUAL FRAMES FOR DISTRIBUTED LIST-MODE TIME-OF-FLIGHT RECONSTRUCTION WITH CONTINUOUS BED MOVEMENT

CROSS REFERENCE TO RELATED APPLICATIONS

This application is a national filing of PCT application Serial No. PCT/IB2013/056301 filed Jul. 31, 2013, published as WO 2014/024099 A2 on Feb. 13, 2014, which claims the benefit of U.S. provisional application Ser. No. 61/681,659 filed Aug. 10, 2012, which is incorporated herein by reference.

The following relates generally to medical imaging. It finds particular application in conjunction with Positron Emission Tomography (PET), image reconstruction, and continuous bed motion (CBM), and will be described with particular reference thereto. However, it will be understood that it also finds application in other usage scenarios and is not necessarily limited to the aforementioned application.

In PET imaging, detector arrays detect pairs of gamma photon's emitted from a positron annihilation event in a subject. The pairs of detected gamma photon's determine a line of response (LOR). A time-of-flight (TOF) PET adds an estimate of the originating location where the annihilation event occurred based on the mean time difference between detection of each photon pair. The estimate is a distance along the LOR. Detected coincident pairs and TOF information can be recorded in an event list called list mode data. One or more images are reconstructed from the list mode data.

Clinical workflow includes the time to scan the patient and the time to reconstruct one or more images. Clinical time is valuable. Clinical workflow can include imaging with one or more imaging modalities such as X-ray computed tomography (CT). One approach to improving clinical workflow is to generate images quickly while reducing overall scan time. When imaging a region of the patient, which is longer than the imaging region of the scanner, a step and shoot technique has been used to generate an elongated image. The patient support moves to a first position, stops, and a first region of the patient is imaged. After imaging the first region, the support is moved to a second position, stopped, and a second region is imaged, and so forth. For uniform sampling, the regions of the patient are overlapped, e.g. by 50%. However, the time to move or step to a next position prolongs the overall scan time. The stopping/starting motion is uncomfortable to some subjects. In multi-modal or hybrid systems, such as PET-CT, some modalities, such as CT, do not benefit from the step and shoot method which may actually hinder the workflow of the other modality.

Another approach is continuous bed movement (CBM). The CBM shortens the overall scan time because the bed is in continuous motion and data is collected continuously. The time to start and stop the bed in the step and shoot method is eliminated. However, a single large data set is collected and image reconstruction is deferred until all data is acquired. For example, in sinogram based reconstruction of the elongated data set, each sinogram includes data contributions from the full length of the data set. Thus, the data cannot be binned into sinograms until all the data is collected. Thus, while the overall data acquisition time for PET can be reduced, the image reconstruction is deferred until the end which uses intensive computing resources. Typically, the patient is not released from the scanner until the reconstructed image has been received and approved causing a bottleneck in the workflow. Additionally, combining the reconstructed images with images from other modalities is deferred which adds to the computing resource bottleneck. The combination with other modalities utilizes imaging components such as attenuation maps.

The following discloses a new and improved virtual frames for distributed list-mode reconstruction with continuous bed movement which addresses the above referenced issues, and others.

In accordance with one aspect, a positron emission tomography (PET) system includes a memory, a subject support, a categorizing unit, and a reconstruction unit. The memory continuously records detected coincident event pairs detected by PET detectors. The subject support supports a subject and moves in a continuous movement through a field of view of the PET detectors. The categorizing unit categorizes the recorded coincident pairs into each of a plurality of spatially defined virtual frame. The reconstruction unit reconstructs the categorized coincident pairs of each virtual frame into a frame image and combines the frame images into a common elongated image.

In accordance with another aspect, a method of positron emission tomography (PET) includes moving a subject on a subject support continuously through a field of view of PET detectors while recording detected coincident event pairs in a memory. Recorded coincident event pairs are categorized into each of a plurality of spatially defined virtual frames. The categorized coincident events of each virtual frame are reconstructed into a common elongated image.

In accordance with another aspect, a time-of-flight (TOF) positron emission tomography (PET) system includes a PET detector array, a subject support, and one or more processors. The PET detector array detects and records coincident events in a list mode. The subject support supports a subject and moves in a continuous movement through a field of view of the PET detector array. The one or more processors are configured to categorize the recorded coincident pairs into contiguous virtual frames based on time-of-flight information. The one or more processors are further configured to reconstruct a frame image from each virtual frame and combine frame images into a continuous elongated field of view.

One advantage is improved patient comfort.

Another advantage resides in integrated multi-modal workflow.

Another advantage resides in efficient concurrent reconstruction with distributed processing.

Another advantage includes shorten scan latency.

Another advantage is a uniform axial sensitivity profile.

Another advantage resides in better axial sampling and spatial resolution.

Another advantage includes region of interest adapted acquisition.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a CBM with virtual frames PET system.

Figure 2:
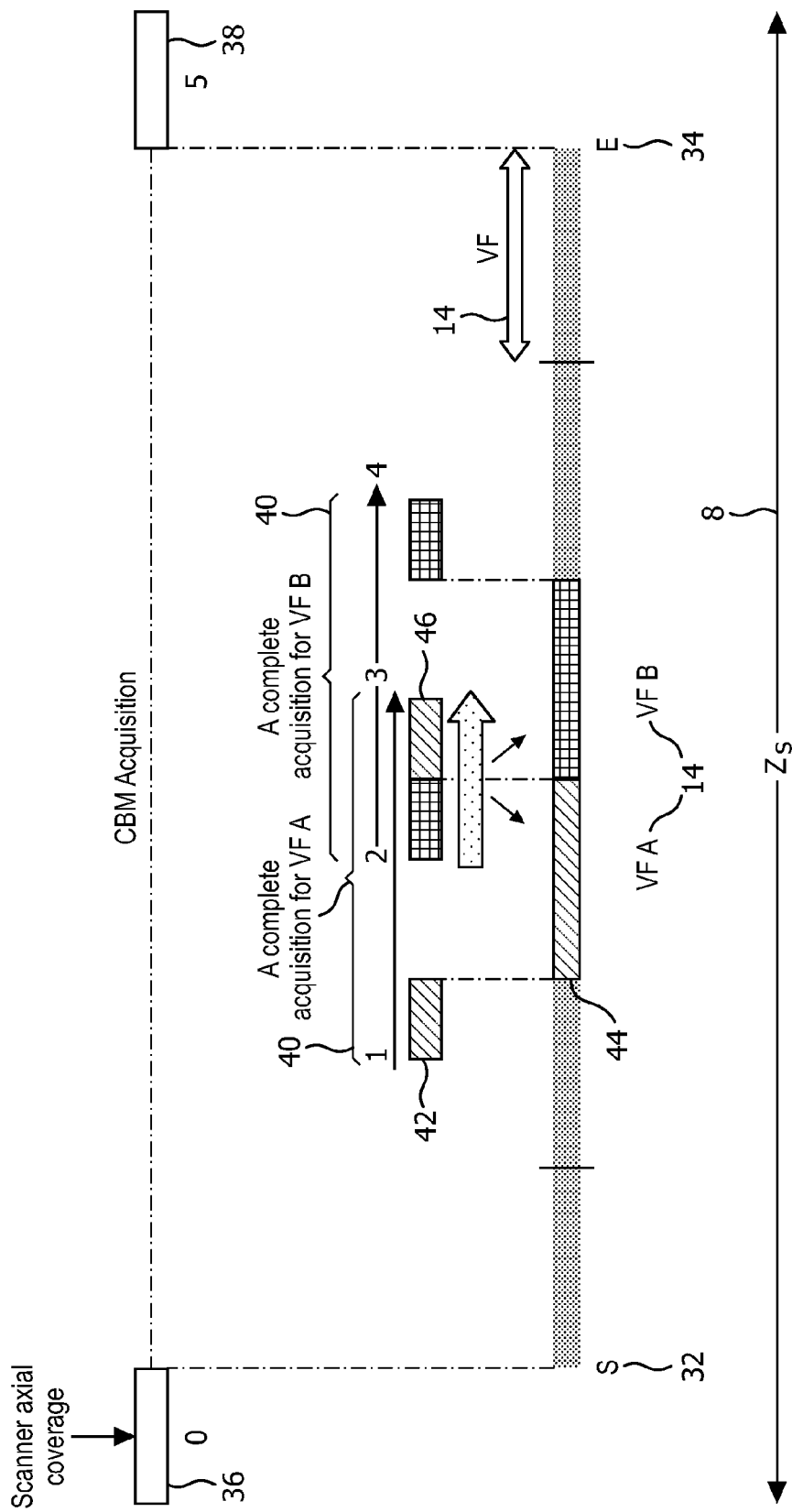

FIG. 2 schematically illustrates an exemplary CBM acquisition with virtual frames.

Figure 3:
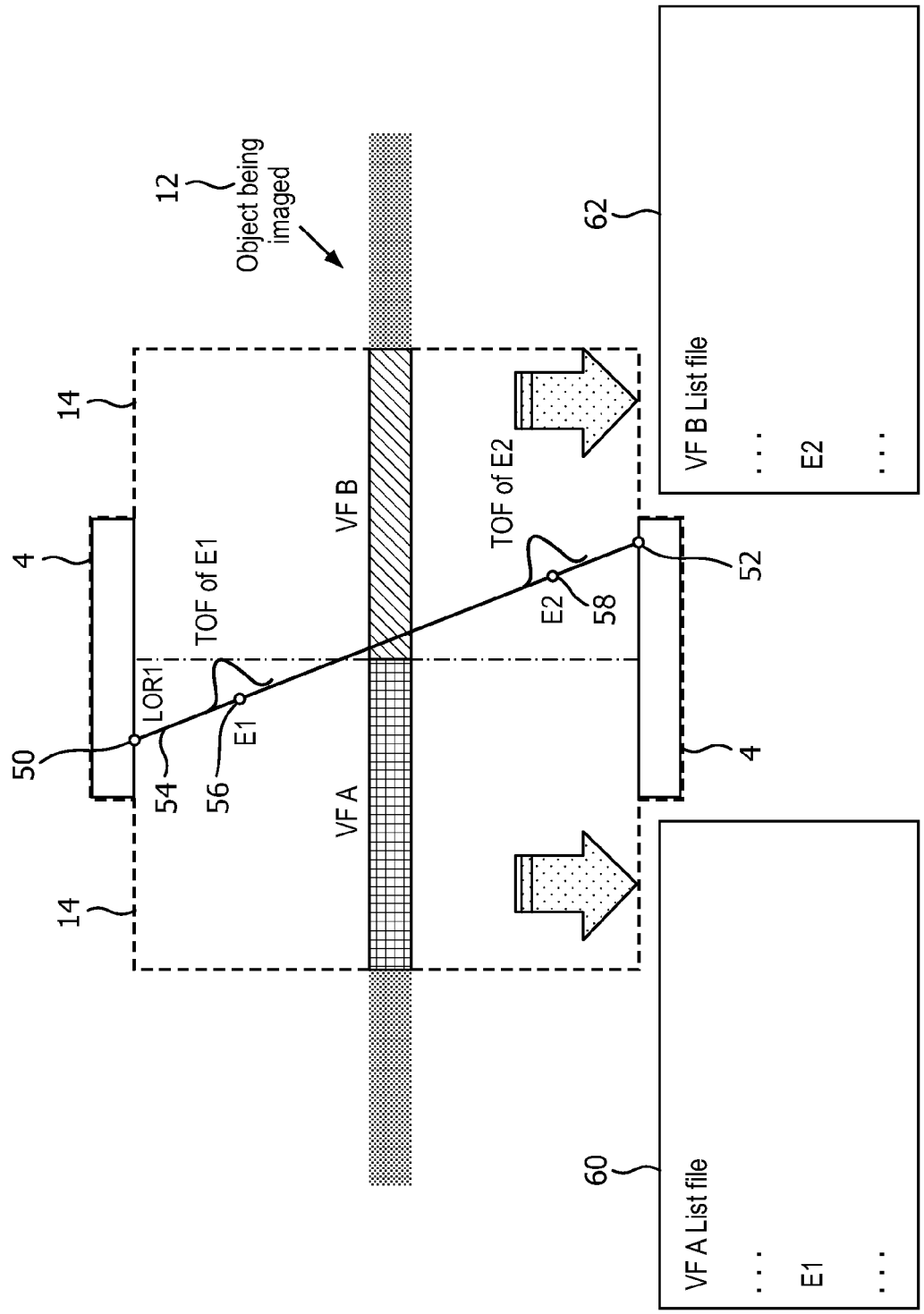

FIG. 3 schematically illustrates an exemplary CBM using time-of-flight (TOF) virtual frame categorization of events.

Figure 4:
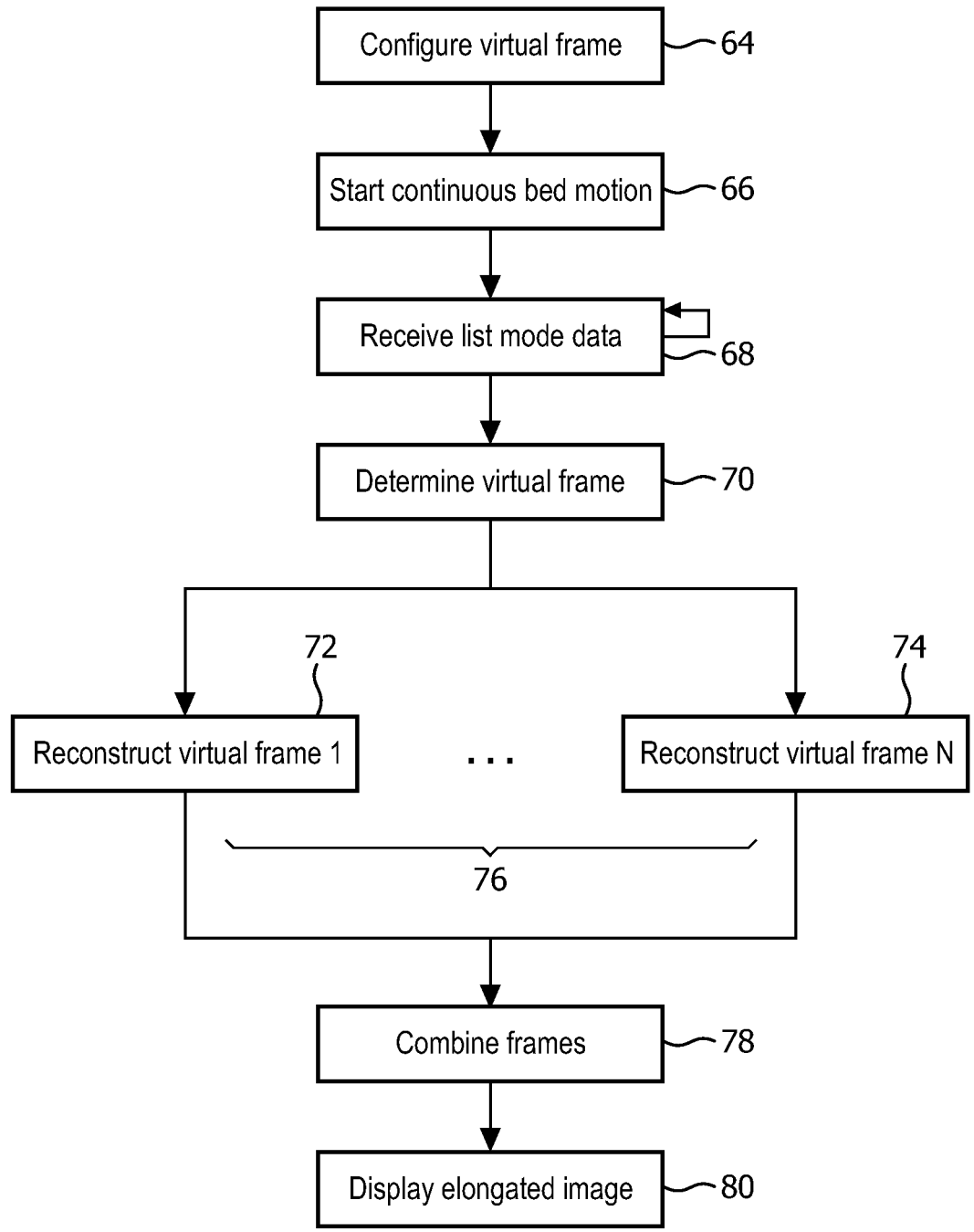

FIG. 4 flowcharts one method of using an embodiment of CBM with virtual frames.

With reference to FIG. 1, an embodiment of a CBM with virtual frames TOF-PET system (1) is schematically illustrated. The system 1 includes a TOF-PET scanner 2 shown in a cross section. A non-TOF PET is also contemplated. The scanner is configured with a subject support or bed 3 which moves in a continuous movement through a PET detector array 4. The detectors are disposed about an opening or bore 6 through which the subject support moves in an axial direction 8. The disposition of the detectors 4 about the opening define a field of view 10. The subject support 3 supports a subject 12 who is injected with a radiopharmaceutical. As the subject support 3 moves through the field of view 10, the radiopharmaceutical decays as it is taken up by tissue then washes out. As the radiopharmaceutical decays, positrons are emitted which cause annihilation events that emit gamma photons as coincident pairs. The coincident pairs of gamma photons from the field of view 10 are detected by the detectors 4. The CBM or movement of the subject support is recorded such as an initial position, constant speed and elapsed time, and/or by positional sensors which record the exact position at a time $t_i$ synchronized with the detectors. The data for each detector event includes the time each event of the pair was detected, a detector location at which each event was detected, and support location at the time of detection.

The volume or subject to be imaged 12 is divided into contiguous spatial virtual frames 14 defined by a distance along the axial direction of the movement of the subject support. The virtual frames 14 can be any length and are configured by a framing unit 16. The length of each virtual frame 14 configured by the framing unit 16 can be based on a variety of factors such as a protocol of a scan, a length of the field of view, a distributed computing configuration, a velocity of the subject support, an expected image quality, anatomical features of the subject from another imaging modality and the like. For example, one frame may be sized to the brain, and another frame to the heart, another to the abdomen, etc. The frames can be longer, shorter, or the same size as the field of view 10. In another example with many distributed processors, many virtual frames can be used to distribute the reconstruction workload. With a high rate of speed for the subject support, longer virtual frames are indicated.

The detected coincident pair events are recorded in list mode. The detectors 4 are connected to a list mode memory 18 which records the coincident pair events in order. The list mode includes the time and location of each detected gamma photon, from which time-of-flight information is derived. Event data is acquired continuously in the list mode as the subject support 3 moves continuously through the field of view 10. Each virtual frame 14 moves into the field of view, through the field of view, and passes out of the field of view. The list mode memory can be either transitory or non-transitory. The non-transitory memory includes storage mediums such as disk, virtual disks, cloud based storage and the like.

A categorizing unit 20 categorizes the coincident pairs into one of a virtual frame 14 based on a spatial location at which the annihilation decay event occurred. The categorization includes a translation from the coordinate system of the detectors to the coordinate system of the subject support. If the subject does not move, then the subject support and the subject shared the same coordinate system. The two coordinate systems share the same planar position or x-y coordinate and differ only in the z or axial direction. The categorization resolves the difference between the $z_d$ or detector coordinate and the $z_s$ or subject support coordinate. The resolution can be performed using the time from the list mode and the relative position of the subject support at the same time. The relative position of the subject support is determined from initial position, velocity and elapsed time, and/or sensors which determine a position at a point in time. For example, with an initial position time to, coordinate position $z_s=0$, and speed of 10 mm/s at time $t_i=50$ s the relative coordinate position is $z_s=500$ mm. If the initial coordination position of $z_s=z_d$ for an initial position. Then the $z_s$ coordinate position of event which occurred at time $t_i$ is given by $z_d+500$ mm. Alternatively, if the position of the $z_s$ is known at time $t_1$ and $t_2$ and an acquisition timestamp indicates that the time of the event occurred at $t_d$ where $t_1<t_d<t_2$ and the speed is relatively constant, then the position $z_s$ can be interpolated at time $t_d$.

Each coincident pair can be categorized in real time as the pair is received or retrospectively from the list mode memory. The categorization can include adding an index identifying its virtual frame to the coincident pair in list mode memory, and/or sorting the coincident pair into the corresponding separate list for each virtual frame 21. Note that the coincident pair events are categorized by spatial location, not by time of detection. Particularly when an interface between two frames is moving through the field of view, the events of the two adjoining frames will be temporally interspersed.

Once the virtual frame has passed from the field of view, then no more coincident event pairs can be recorded for the virtual frame. Once all the coincident pairs present in the list mode memory at or before the time each virtual frame passes from the field of view are categorized, then that virtual frame can be reconstructed. Each virtual frame can be reconstructed separately by a reconstruction unit 22. The reconstruction unit 22 reconstructs each virtual frame with the coincident pairs categorized for the respective virtual frame. The virtual frame represents a complete unit of work for reconstruction which can utilize distributed processing techniques. For example, a first virtual frame can be assigned to a first processor configured to perform the reconstruction, such as Cartesian based reconstruction, sinogram based reconstruction, or the like. While the first processor reconstructs the first frame into an image, data is continually acquired for subsequent virtual frames. As the data for the second virtual frame becomes available by the frame passing from the field of view and the coincident pairs categorized, a second processor is assigned reconstruction of the second virtual frame. As reconstruction of each virtual frame into an image completes, then the processor can be reassigned to another virtual frame reconstruction. Processors can include multi-core processors and multiple processors and/or combinations.

As the reconstruction unit completes reconstructing each virtual frame into an image, the frame image is combined with the other reconstructed images of the elongated image and can be displayed on a display device 24 such as a display device of a workstation 26. The display device can include a computer monitor, a television screen, a touch screen, Cathode ray tube (CRT), Flat panel display, Light-emitting diode (LED) displays, Electroluminescent display (ELD), Plasma display panels (PDP), Liquid crystal display (LCD), Organic light-emitting diode displays (OLED), a projector, and the like. The workstation 26 includes an electronic processor or electronic processing device 28, and one or more input devices 30. The display 24 displays the elongated reconstructed image or each virtual frame, and menus, panels, and user controls, such as entry or selection of configuration information utilized by the framing unit 16. The workstation 20 can be a desktop computer, a laptop, a tablet, a mobile computing device, a smartphone, and the like. The input device can be a keyboard, a mouse, a microphone, and the like. The various units 16, 20, 22 are suitably embodied by an electronic data processing device programmed to perform the function of the various units, and can include an electronic processor or electronic processing device 28 of the workstation 26, or by a network-based server computer operatively connected with the workstation 26 or so forth. Moreover, the disclosed framing, categorizing, and reconstruction techniques are suitably implemented using a non-transitory storage medium storing instructions (e.g., software) readable by an electronic data processing device and executable by the electronic data processing device to perform the disclosed framing, categorizing and reconstruction techniques. Alternatively, the images of each virtual frame can be reassembled into an image volume and stored in a storage management system such as a Picture Archiving and Communication Systems (PACS), Radiology Information System, and the like.

FIG. 2 schematically illustrates an exemplary CBM acquisition with virtual frames 14. The volume of a subject to be imaged starts at a starting point 32 and ends at an ending point 34. The volume is divided into contiguous virtual frames 14. Data acquisition or axial scanner coverage extends from an initial time 36 as the leading edge of the first frame enters the field of view to an end time 38 as the trailing edge of the last frame passes from the field of view. A complete data acquisition 40 for each virtual frame 14 includes a leading component 42, main component 44, and a trailing component 46. The leading component includes LORs which include one end point within the virtual frame and one in a leading frame. The main component includes LORs with both end points in the virtual frame, and the trailing component with one end point in the virtual frame and one in a following frame. The geometry of the detectors affects the length of the leading and trailing components. The size of the bore and the axial span of the detectors determine possible LORs. Many LORs occur at angles not orthogonal to the axis of movement. Thus, LORs can cross virtual frames, which means that data acquisition overlaps between frames.

FIG. 3 schematically illustrates an exemplary CBM with TOF virtual frame categorization of the coincident event pairs that span two frames. The coincident detected event pair of a first 50 and a second 52 detected gamma photon define end points of a line of response (LOR) 54. A position of an annihilation event, such as E1 56 or E2 58 which emitted the detected gamma photon's occurs along the LOR, is resolved by the time of flight information. The TOF information provides information to determine the location or a probabilistic curve of a range of locations along the LOR at which the annihilation event occurred. The relative position of the subject support using the synchronized time and/or position of the subject support provides the translation to the coordinate system of the subject support. Thus, the time of flight provides the estimate which determines in the example the event occurred at a location E1 or at a location E2. In the instance of occurring at E1, the recorded coincident event is categorized in virtual frame A by resolving the coordinate difference between the detector and subject support. In the instance of occurring at E2, the recorded coincident event is categorized in virtual frame B. Categorization is performed by the categorization unit 20.

Gamma photon pairs are located based on the position in the coordinate system of the subject support. This includes the coordinate system of the subject who is not moving relative to the subject support. Gamma photon pairs are detected as coincident pairs by the detectors in the coordinate system of the detectors. Categorization resolves the difference between the two coordinate systems. In the instance of when the TOF information indicates the event occurring at a frame boundary, then the event can be resolved by either categorizing the event in both frames and weighting the boundary in the reconstruction for overlap, categorizing according to the leading edge, categorizing according to the trailing edge, etc.

Categorization can include adding an identifier such as an index to the list mode data and/or sorting the list mode data into separate lists. Separate lists can be used to reduce file contention prevention and improve data access during reconstruction. In the example, the E1 event sorts into a list file for virtual frame A 60 and the E2 event sorts into a list file for virtual frame B 62 based on the axial coordinate at a time t. Each list of virtual frame A 60 and virtual frame B 62 includes the categorized coincident pairs or events for the respective virtual frame.

Rather than TOF, events could be categorized in other ways, particularly if TOF information is not available. In one example, the annihilation event is assigned to the frame which is traversed by the largest portion of the LOR. In another example, the annihilation event is assigned proportionally to both frames, e.g. based on LOR portion.

FIG. 4 flowcharts one method of using an embodiment of CBM with virtual frames. In a step 64 the virtual frames 14 are configured by the framing unit 16. The configuration of the virtual frames defines the length of the virtual frame along the axial direction 8 of the CBM. The virtual frames 14 are configured based on input from the healthcare practitioner, the subject medical record, configuration information for the TOF-PET scanner, distributed computing resources, etc.

After administering the radiopharmaceutical, and placement of the subject 12 on the subject support 3, the healthcare practitioner initiates start of the continuous bed movement (CBM) or movement of the subject support in a step 66. The subject support moves in a continuous motion and preferably at a substantially constant speed. Positional sensors and/or time determine the precise position of the subject support and the virtual frames. The continuous motion provides for patient comfort over step and shoot techniques.

In a step 68, the system continuously receives detected coincident pairs that define LORs in list mode. The detected coincident pairs include time of flight information. The detected coincident pairs are recorded in the list mode memory. While the subject support is in motion, the system can receive the detected data continuously. The CBM through the detectors along the axial position provides a more uniform axial sensitivity profile. The sampling along the axial length which passes through the detectors provides better axial sampling and spatial resolution. In an alternative embodiment, the information from other modalities such as CT is used to define the virtual frame to begin acquisition for region of interest adapted acquisition.

The recorded coincident pairs in list mode memory 18 are categorized in a step 70 by the categorization unit 20. The categorization can begin as soon as each coincident pair event is recorded in the list mode memory 18 and continues as events are added to the memory. The categorization resolves the difference between the coordinate system of the detectors 4 and the subject support 3 and categorizes the event into the virtual frame in which the annihilation event was determined or projected to have occurred. The categorized virtual frame can include an identifier added to the list mode memory or the categorized virtual frame can include sorting the event into the separate list for each virtual frame, respectively.

As the virtual frame 14 leaves the field of view 10 of the detectors 4, data acquisition for the virtual frame ends. In a series of concurrent steps 70, the reconstruction unit 22 reconstructs each categorized virtual frame. Reconstruction of each frame uses the separate list of each virtual frame or the index of identifiers into the list mode memory. For example a first virtual frame is reconstructed in a step 66, and a final virtual frame N is is reconstructed separately in step 68. Reconstructing the virtual frames separately provides for distributed computing techniques to be applied for reducing computing bottlenecks and efficient concurrent image reconstruction. The information such as attenuation maps from other modalities can be applied to each concurrent reconstruction.

As each concurrent reconstruction ends, the reconstructed image of each virtual frame is optionally displayed on the display device 24 in a series of concurrent steps 76. For example as the reconstruction of the first virtual frame 66 ends, the image of the first virtual frame is displayed on the display device in a step 72. Subsequent virtual frames can be displayed side by side, in overlay, etc. The display can continue for each virtual frame ending with a final virtual frame N in a step 74. The frames are reassembled 78 into a continuous elongated image. The elongated image displayed, stored in patient archives, and the like. The healthcare practitioner can interact with the system using the input device 30.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A positron emission tomography (PET) system comprising:
   a memory configured to continuously record detected coincident event pairs detected by PET detectors;
   a subject support configured to support a subject and move in a continuous movement through a field of view of the PET detectors;
   a categorizing unit configured to categorize the recorded coincident event pairs into each of a plurality of spatially defined virtual frames, wherein the detected events of some of the detected coincident event pairs are located in two different virtual frames and the categorizing unit allocates the coincident event pair to one of the two virtual frames based on at least one of time-of-flight information and a projected location of an annihilation event which produced the event pair; and
   a reconstruction unit configured to reconstruct the categorized coincident pairs of each virtual frame into a frame image and combine the frame images into a common elongated image.

2. The system according to claim 1, further including:
   a framing unit which configures contiguous virtual frames along a length along an axis of the subject support movement.

3. The system according to claim 2, wherein the length of the configured virtual frame is based on at least one of:
   a protocol of a scan;
   a field of view length;
   a distributed computing configuration;
   a velocity of the subject support;
   an image quality; and
   subject anatomical features.

4. The system according to claim 1, wherein the categorizing unit categorizes at least one of the coincident event pairs that have detected events in two different virtual frames into one of the two virtual frames based on the time-of-flight information.

5. The system according to claim 1, wherein the categorizing unit categorizes at least one of the coincident event pairs that have detected events in two different virtual frames into one of the two virtual frames based on the projected location of the annihilation event which produced the event pair.

6. The system according to claim 1, wherein a position of each virtual frame is determined based on initial position and velocity of the subject support and a time of the coincident pair.

7. The system according to claim 1, wherein the reconstruction unit is further configured to reconstruct each virtual frame independently.

8. The system according to claim 1, further including:
a display device configured to display the elongated image, the elongated image growing as each virtual frame construction is completed.

9. The system according to claim 1, wherein the reconstruction unit is configured to start reconstructing each frame image as the virtual frame passes from the field of view.

10. A method of positron emission tomography (PET), comprising:
moving a subject on a subject support continuously through a field of view of PET detectors while recording detected coincident event pairs in a memory;
categorizing recorded coincident event pairs into each of a plurality of spatially defined virtual frames, wherein the categorizing includes allocating coincident pairs to one of two virtual frames where the detected coincident event pair is located in two different virtual frames;
reconstructing the categorized coincident events of each virtual frame into a common elongated image.

11. The method according to claim 10, further including:
starting reconstruction of each frame image as a corresponding virtual frame passes from the field of view.

12. The method according to claim 11, wherein configuring the length of the plurality of virtual frames is based on at least one of:
a protocol of a scan;
a field of view length;
a distributed computing configuration;
a velocity of the subject support;
an image quality; and
subject anatomical features.

13. The method according to claim 10, wherein coincident event pairs detected events in two different virtual frames are categorized based on time-of-flight information.

14. The method according to claim 10, wherein coincident event pairs have detected events in two different virtual frames are categorized based on a projected location of an annihilation event which produced the event pair.

15. The method according to claim 10, further including:
displaying the elongated image which grows as each frame construction completes on a display device.

16. A non-transitory computer-readable storage medium carrying software which controls one or more electronic data processing devices to perform the method according to claim 10.

17. An electronic data processing device configured to perform the method according to claim 10.

18. A time-of-flight (TOF) positron emission tomography (PET) system, comprising:
a PET detector array which detects and records coincident events in a list mode;
a subject support which supports a subject and moves in a continuous movement through a field of view of the PET detector array; and
one or more processors configured to:
categorize the recorded coincident event pairs in one of a plurality of spatially defined virtual frames when the coincident events of one of the coincident event pairs are categorized into contiguous virtual frames, allocating both of the coincident events to a common virtual frame based on time-of-flight information;
reconstruct a frame image from each virtual frame; and
combine frame images into a continuous elongated image.

19. A time-of-flight (TOF) positron emission tomography (PET) system, comprising:
a PET detector array configured to detect coincident events;
a memory configured to record pairs of the detected coincident events in a list mode;
a subject support configured to support a subject and move the subject in a continuous movement through a field of view of the PET detector array; and
one or more processors configured to:
categorize each recorded coincident event pair in which both events of the coincident event pair correspond to a common virtual frame into the common virtual frame;
allocate coincident event pairs in which each event of the coincident event pair corresponds to different virtual frames to a common one of the different virtual frames, such that each of the coincident event pairs that correspond to different virtual event frames is categorized in the common virtual frame;
reconstruct a frame image from each virtual frame; and
combine frame images into a continuous elongated image.

20. The system according to claim 19, wherein the coincident event pairs in which each event of the coincident event pair corresponds to different virtual frames are allocated based on time-of-flight information.

21. The system according to claim 19, wherein the coincident event pairs in which each event of the coincident event pair corresponds to different virtual frames are allocated based on a projected location of an annihilation event which produced the coincident event pair occurred.

* * * * *